United States Patent
Makhotkin et al.

(10) Patent No.: US 10,416,101 B2
(45) Date of Patent: Sep. 17, 2019

(54) MODEL INDEPENDENT GRAZING INCIDENCE X-RAY REFLECTIVITY

(71) Applicant: Malvern Panalytical B.V., Almelo (NL)

(72) Inventors: Igor Alexandrovich Makhotkin, Almelo (NL); Sergey Yakunin, Almelo (NL)

(73) Assignee: Malvern Panalytical B.V., Almelo (NL)

(*) Notice: Subject to any disclaimer, the term of this patent is extended or adjusted under 35 U.S.C. 154(b) by 139 days.

(21) Appl. No.: 15/853,257

(22) Filed: Dec. 22, 2017

(65) Prior Publication Data

US 2018/0180561 A1 Jun. 28, 2018

(30) Foreign Application Priority Data

Dec. 22, 2016 (EP) .................... 16206361

(51) Int. Cl.
*G01N 23/201* (2018.01)
*G01N 23/20* (2018.01)

(52) U.S. Cl.
CPC ....... *G01N 23/20* (2013.01); *G01N 2223/052* (2013.01); *G01N 2223/61* (2013.01)

(58) Field of Classification Search
CPC ... A61B 17/3423; A61B 17/3439; A61B 1/05; A61B 2017/00199; A61B 2017/00557; A61B 2017/00858; A61B 34/35; A61B 34/70; A61B 90/361; A61B 90/37; G01N 2223/052; G01N 2223/61; G01N 23/20; G01N 2223/633; G01N 2223/634; G01N 23/223; G01N 23/2252; G01N 33/54373; G01N 23/201; G01N 2021/8438; G01N 21/211; G01N 21/274; G01N 21/33; G01N 21/8422; G01N 21/94; G01N 21/9501; G01N 2223/076; G01N 2223/1006;

(Continued)

(56) References Cited

U.S. PATENT DOCUMENTS 7,039,161 B2 * 5/2006 Ito .................... G01N 23/201
378/70
7,120,228 B2 * 10/2006 Yokhin ............ G01N 23/20008
378/90

(Continued)

OTHER PUBLICATIONS

Model-independent method for reconstruction of scattering-length-density profiles using neutron or x-ray reflectivity data, Xiao-Lin Zhou and Sow-Hsin Chen, Physical Review E, vol. 47, No. 5, pp. 3174 to 3190, Jun. 1993.

(Continued)

*Primary Examiner* — Irakli Kiknadze
(74) *Attorney, Agent, or Firm* — Leason Ellis LLP

(57) ABSTRACT

A method of measuring properties of a thin film stack by GIXR divides the stack into sub-layers and represents the composition of each sub-layer by an number P. The numbers P represent the composition of each layer. For example, integers may represent pure material and fractional values represent mixtures of the adjacent pure materials. This representation is then used to fit to measured data and the best fit gives an indication of the material composition of each of the sub-layers and hence as a function of depth.

11 Claims, 6 Drawing Sheets

(58) Field of Classification Search
CPC ............. G01N 23/20008; G21K 1/062; G21K 2201/061; G21K 1/067; G02B 5/0891
USPC ................................................ 378/70, 86–90
See application file for complete search history.

(56) References Cited

U.S. PATENT DOCUMENTS

| | | | |
|---|---|---|---|
| 7,130,376 B2* | 10/2006 | Berman | G01B 15/02 |
| | | | 378/82 |
| 8,513,603 B1* | 8/2013 | Lederman | G01N 23/223 |
| | | | 250/305 |
| 2014/0078486 A1* | 3/2014 | Yakunin | B82Y 10/00 |
| | | | 355/71 |
| 2014/0168758 A1* | 6/2014 | Rose | G02B 5/0891 |
| | | | 359/359 |

OTHER PUBLICATIONS

Andrey Zameshin et al: "Reconstruction of interfaces of periodic multilayers from X-ray reflectivity using a free-form approach", Journal of Applied Crystallography, vol. 49, No. 4, Jul. 20, 2016 (Jul. 20, 2016), pp. 1300-1307, XP055373942, DOI: 10.1107/S160057671601044X * the whole document *.

David L. Windt: "IMD-Software for modeling the optical properties of multilayer films", Computers in Physics., vol. 12, No. 4, Jan. 1, 1998 (Jan. 1, 1998), p. 360, XP055241853, US, ISSN: 0894-1866, DOI: 10.1063/1.168689 * the whole document *.

* cited by examiner

MODEL INDEPENDENT GRAZING INCIDENCE X-RAY REFLECTIVITY

CROSS-REFERENCE TO RELATED PATENT APPLICATIONS

The present application claims priority under 35 U.S.C. § 119 to European Patent Application No. 16206361.4, filed Dec. 22, 2016, which is hereby incorporated by reference in its entirety.

FIELD OF INVENTION

The application relates to methods for the analysis of grazing incidence X-ray reflectivity data.

BACKGROUND TO THE INVENTION

In order to measure properties of ultrathin films, e.g. film thickness, densities and roughness, using X-rays, X-rays may be passed through the sample at grazing incidence angles nearly parallel to the surface of the film. Multiple measurements are taken at different angles. Calculations are then carried out to determine properties of the sample from the measured results. Such a measurement is referred to as grazing incident X-ray reflectivity, abbreviated as GIXRR or GIXR or XRR. In this application, GIXR will be used.

The direct determination of thin film properties from GIXR data is not possible therefore the parameters of studied films have to be determined by fitting of a simulated (calculated) GIXR curve to a measured curve. The parameters of the simulated GIXR curve are adjusted such that mismatch between measured and simulated data is minimal. One approach, for calculations is to use the model which has a plurality of layers, each with a film thickness, density, and interface roughness {Windt, 1998 #109}.

This approach can work well in certain circumstances, in particular if the thin film has thin interfaces and the layers have constant density. However, in the majority of cases thin films grown by physical sputtering techniques can form chemical compounds at the interfaces, and further the thickness of the interface can be comparable to the thickness of the film.

Another example where this method can fail is in the case of relatively thick films which do not have a constant density profile.

To analyse films with low absorption a "groove tracking method" can be used. This assumes that the sample has a set of thin sublayers, each of which has a thickness much less than the actual thickness of each of the sub-layers. Each of the j sublayers has a corresponding refractive index $n_j$. The calculation varies the real part of refractive index of each of the sublayers until the best possible match to the observed results is obtained.

See in particular the paper "Model-independent method for reconstruction of scattering-length-density profiles using neutron or x-ray reflectivity data", Xiao-Lin Zhou and Sow-Hsin Chen, Physical Review E, Volume 47, Number 5, pages 3174 to 3190, June 1993 for a description of the method.

However, this approach also has problems. Calculations by the groove method are not wholly reliable and in particular the method can produce many unphysical solutions, i.e. the calculations can converge on a result that does not match physical reality.

There is accordingly a need for an improved method of measuring properties of ultrathin films.

SUMMARY OF THE INVENTION

According to a first aspect of the invention there is provided a method of measuring properties of a thin film stack made up of known physical materials and interfaces between the physical materials, the method comprising:
defining an ordered list of the plurality of physical materials in the stack, and defining for each physical material a respective defined index value, wherein the defined index values monotonically increase or monotonically decrease along the ordered list;
capturing a measured grazing index X-ray reflectivity curve of intensity against angle for a range of angles; and
setting up an array of N sub-layers (i) representing the thin film stack, each element of the array of sub-layers having a defined parameter $P_j$ representing the composition of that sub-layer;
fitting the parameters $P_j$ so that a calculated grazing incidence X-ray reflectivity curve against angle as a function of the parameters $P_j$ most accurately matches the measured grazing index X-ray reflectivity curve against angle over the range of angles to obtain fitted parameters $\tilde{P}_j$;
and outputting a measure of the composition of the thin film stack based on the fitted parameters $\tilde{P}_j$;
wherein the parameters $P_j$ have values that are defined:
(a) to represent the respective physical material when the parameter $P_j$ has one of the defined index values; and
(b) when the value $P_j$ lies between a pair of defined index values, to represent a composition that is a mixture of the physical materials of the pair of index values, the value of $P_j$ monotonically changing from the index value of a first physical material of a pair to the index value of the other physical material of the pair as the composition changes from pure first physical material to pure second physical material.

The inventors have realised that a problem with the existing groove tracking method is that the refractive indices $n_j$ are assumed to be real, and therefore the method is not appropriate where significant X-ray absorption takes place, resulting in imaginary components to the refractive index.

However, by using the approach of the invention and defining the parameters $P_j$, a single parameter for each sub-layer takes into account both the real and imaginary parts of the optical constant without an excessive number of free parameters. Since excessive parameters can result in poor performance and difficulties in reliable fitting, the method according to the invention can achieve a good fit even in the case that there is significant absorption in one or more of the layers.

Note that the method may output the Pj values themselves, which directly relate to the composition of each sub-layer, a composition obtained directly from the $P_j$ values, and/or some other property that may be calculated from the $P_j$ values such as the optical constants (real and imaginary part of refractive index) as a function of depth.

In a preferred arrangement the defined index values are integers representing the position of the physical material in the list, and non-integer values x represent a composition having a fraction (1-frac ($P_j$)) of the material represented by the index value |x|; and
a fraction frac ($P_j$) of the material represented by the index value |x|+1.

In this way, integer values of the parameters represent pure materials and fraction values represent combinations of materials.

The step of fitting the parameters $P_j$ may be carried out by minimising the value of the sum of squares of the residuals obtained by subtracting the measured grazing index reflective curve from the calculated grazing index reflectivity curve for each measured angle.

In particular, the step of fitting the parameters $P_j$ represented as a vector P may comprise minimising the value of $$\chi^2 = \frac{1}{N-l}\left(\sum_\theta u^2(\theta, P)\right), \text{ where } u(\theta, P) = \frac{I_{calc}(\theta, P) - I_{exp}(\theta)}{\sigma(\theta)},$$

where N is a number of measured data points, θ is the angle of incidence in GIXRR measurements, $I_{calc}(\theta, P)$ is the calculated intensity of GIXRR, $I_{exp}(\theta, P)$ is the measured intensity of GIXRR, σ(θ)—uncertainty of GIXRR measurement, and l is the number of the fit parameters.

The step of fitting the parameters $P_j$ may include fitting the parameters as elements of a vector P, the method comprising minimising the value of $$\chi^2 = \frac{1}{N-l}\left(\sum_\theta u^2(\theta, P)\right) + R_{reg}.$$

$$\text{where } u(\theta, P) = \frac{I_{calc}(\theta, P) - I_{exp}(\theta)}{\sigma(\theta)},$$

where N is a number of measured data points, θ is the angle of incidence in GIXRR measurements, $I_{calc}(\theta, P)$ is the calculated intensity of GIXRR, $I_{exp}(\theta, P)$ is the measured intensity of GIXRR, σ(θ)—uncertainty of GIXRR measurement, and l is the number of the fit parameters; and $$R = \lambda \sum_{i=2}^{N-1} (2p_i - p_{i-1} - p_{i+1})^2$$

where $N_A$ is the length of the vector x, and r is a regularization parameter that specifies the degree of profile smoothness.

A Levenberg Marquardt algorithm may be used to carry out the step of minimising.

The method may provide a representation of the real part of the refractive index for a material represented by $P_j$ as a function of the value of $P_j$ and a representation of the imaginary part of the refractive index for a material represented by $P_j$ as a function of the value of $P_j$;
wherein the calculated grazing index reflectivity values are calculated using the refractive index values obtained from the values of $P_j$ using the representation of the real part and the representation of the imaginary part.

The number of sublayers is within 30% of $N_{opt}$ given by:

$$N_{opt} = \frac{L}{\Delta z_{opt}} \text{ where } \Delta z_{opt} = \frac{1}{2}\frac{2\pi}{q_{max}} = \frac{\lambda}{4\sin\theta_{max}},$$

$\theta_{max}$ is the highest measured angle and K the wavelength of X-rays used.

BRIEF DESCRIPTION OF THE DRAWINGS

Embodiments of the invention will now be described with reference to the accompanying diagrams, in which.

The Figures are schematic and not to scale.

DETAILED DESCRIPTION

Figure 1:
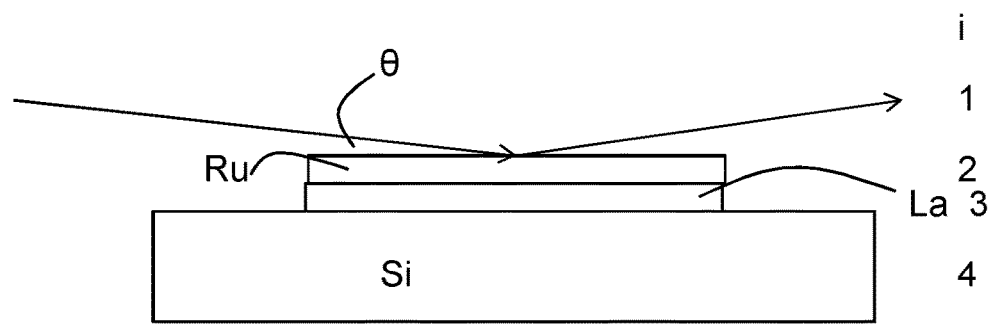
FIG. 1 illustrates grazing index X-ray reflectivity measurement of a sample.

FIG. 1 shows in a conceptual way grazing index X-ray reflectivity measurement of a sample having a layer of Ruthenium on a layer of Lanthanum on a Si substrate. Grazing incidence X-rays are incident on the surface. The intensity of X-rays reflected by the layers is measured as a function of the angle θ, which may vary for example from 0 to 3 or 0 to 7°. Note that the drawing is not to scale—typically the thin layers are only of nanometer scale thickness. The values of i presented in the Figure are used in the calculation as explained later.

Figure 2:
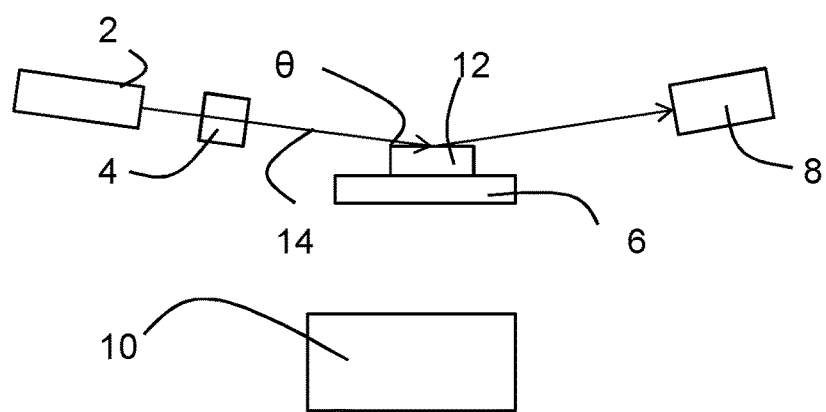
FIG. 2 shows a schematic of apparatus carrying out grazing index X-ray reflectivity.

Referring to FIG. 2, a schematic drawing of apparatus for making such reflectivity measurements on ultrathin films includes an X-ray source 2, collimating optics 4, a sample stage 6 and an X-ray detector 8. The apparatus also includes a computer 10 for controlling the apparatus, and processing data.

In alternative embodiments, multiple computers may be used, for example one computer may control the apparatus and a separate computer used to carry out the processing of the captured data.

In use, a beam 14 of X-rays from the X-ray source are directed by the X-ray optics 4 onto a sample 12 mounted on the sample stage at a grazing incident angle θ. X-rays are reflected to form a reflected X-ray beam and the intensity of the reflected X-ray beam is measured in the X-ray detector 8. The computer adjusts the grazing incident angle to provide a set of intensity values as a function of grazing incident angles over a range of angles.

The intensity of the reflected X-ray beam decreases with increasing angle typically as $\sin(\theta)^{-4}$, and good measurement should be done from close to 0° to an upper angle at which modulations of intensity of the reflected beam are below the measurement nose level and therefore could not be measured. Therefore the range of measured angle is determined by the intensity of incidence X-ray beam and typically is limited to 0 to 5 degrees for a sealed Cu X-ray tube, but for brighter X-ray sources it can be larger.

In order to convert the measured reflectivity as a function of angle the computer contains code for causing the computer to carry out calculations which will now be described in some detail. The input experimental intensity values as a function of angle will be referred to as $I_{exp}(\theta)$ where θ is the angle of incidence.

The calculation method is based on a representation of a thin film stack, i.e. a sequence of thin films. The thin film stack may be represented by a set of material layers, i=1 to a, where a is the number of layers of different material. The value i=0 is used to represent the layer above the thin film stack, i.e. air or vacuum and the values I=1 to a represent an ordered list of different materials.

An example may make this clearer. Consider for example a sample where the sample is known to be made up of a layer of ruthenium, a layer of lanthanum, and a silicon substrate (as illustrated in FIG. 1). The sample is in air. In this case, a=4, as there are three material layers as well as air. The value i=1 represents air, the value i=2 represents ruthenium, the value i=3 represents lanthanum, and the value i=4 represents silicon. The layers are numbered starting from air with i=1, the top exposed layer with a value i=2, and each subsequent layer going down is given the next integer. This is illustrated in FIG. 1.

In order to carry out the calculation, the thin film stack is divided into a larger number of sub-layers j=1 to N, where N is the number of sub-layers, and n is greater than a, each of which is represented as having a refractive index $n_j$ and is defined by a parameter $P_j$. Where the parameter $P_j$ has an integer value, it means that the sub-layer is wholly made up of the material of the $i^{th}$ layer.

Figure 3:
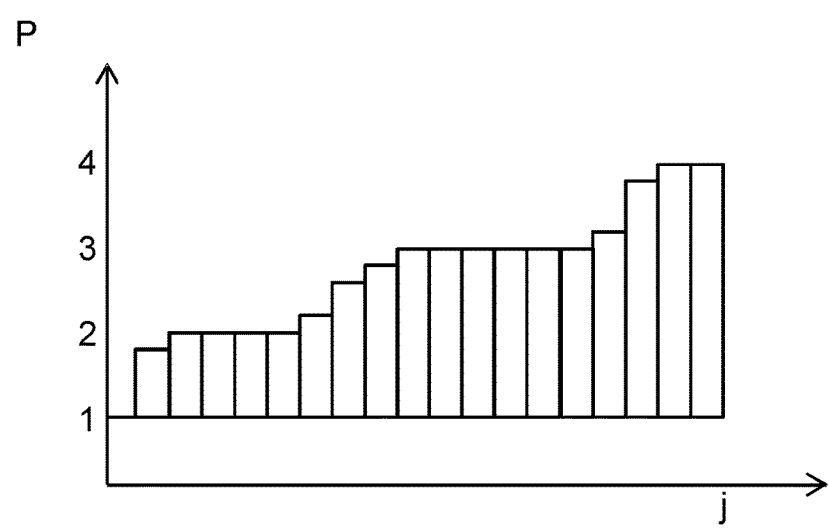
FIG. 3 illustrates P values for a sequence of sub-layers.

A set of sub-layers is illustrated in FIG. 3—note that the y axis relates to the value of P of each layer, the values varying from 1 to 4 corresponding to the arrangement in FIG. 1 above. The lowest layer has a value 1, pure air, followed by an intermediate layer and a number of layers with a value 2, the top layer Ru, followed by three intermediate layers, followed by a number of layers with a value 3, representing La, and then further intermediate layers and layers with a value 4, representing the layer with i=4, the substrate.

For example, if the fourth thin sub-layer has a value $P_4$ of 2, this means that the fourth sub-layer is made up only of the first one of the materials in the ordered list. Keeping with the example above, this would mean that the fourth sub-layer is made of pure ruthenium Non-integer values of $P_j$ represent mixtures with the value of p representing a continuum, between a value. Expressed mathematically, the concentration of the material having an index i given by $|P_j|$ of the $j^{th}$ sub-layer is given by $$\omega_j^A = 1 - \text{frac}(P_j) \tag{1}$$

where | | is the integer function returning the integer part of the argument and frac ( ) is the fractional part function returning the excess beyond the integer part, $$\text{frac}(x) = x - |x|. \tag{2}$$

The remainder of the $j^{th}$ sub-layer is made up of the material indexed by $|P_j|+1$, so the concentration of this material is given by $$\omega_j^B = \text{frac}(P_j). \tag{3}$$

For example, if the eighth sub-layer has a value $P_8$ of 1.1, then the eighth sub-layer is made up of 90% ruthenium (indexed by i=1) and 10% lanthanum (indexed by i=2). If instead the eighth sub-layer has a value $P_8$ of 1.5, then the eighth sub-layer is made up of 50% ruthenium (indexed by i=1) and 50% lanthanum (indexed by i=2). If instead the eighth sub-layer has a value $P_8$ of 1.95, then the eighth sub-layer is made up of 5% ruthenium (indexed by i=1) and 95% lanthanum (indexed by i=2). In the example of FIG. 3, the eighth sub-layer has a value of about 2.7 representing 70% La and 30% Ru.

Thus the values of $P_j$ represent a continuum—as $P_j$ increases from 1 to the highest possible value a, the composition smoothly changes in a monotonic way.

The optical constant $n_j$ of the $j^{th}$ sub-layer has a refractive index can be calculated as following:

$$n_j = 1 - \delta_j - i\beta_j \text{ where} \tag{4}$$

$$\delta_j = 2.7007 \times 10^{-4} \times (\omega_j^A \rho^A + \omega_j^B \rho^B) \left[ \omega_j^A \sum_k \frac{f_k'^A}{\mu_k^A} + \omega_j^B \sum_k \frac{f_k'^B}{\mu_k^B} \right]$$

$$\beta_j = 2.7007 \times 10^{-4} \times (\omega_j^A \rho^A + \omega_j^B \rho^B) \left[ \omega_j^A \sum_k \frac{f_k''^A}{\mu_k^A} + \omega_j^B \sum_k \frac{f_k''^B}{\mu_k^B} \right]$$

are real and imaginary parts of decrement of optical constant. Here
$\rho^A$ and $\rho^B$—are density of pure elements A and B in g/cm3, $f_k^A$ and $f_k^B$—is the atomic scattering factor, and k is the index of chemical element in sub-layers A and B in the layer compound.

In the example k and for Ru and for La is equal to 1. If the layer were to be a compound for example $LaB_6$ then k would change from 1 to 2 where 1 would be for example for La and 2 for B. $\mu_k$—is the molar mass of materials of layers and A and B.

Here density of material sublayer is lineal combination of densities of pure materials but if compounds of materials in layers A and B are known and their density does not coincide with linear combination of densities, that a look up table of correct densities can be generated for a collected compounds.

Figure 4:
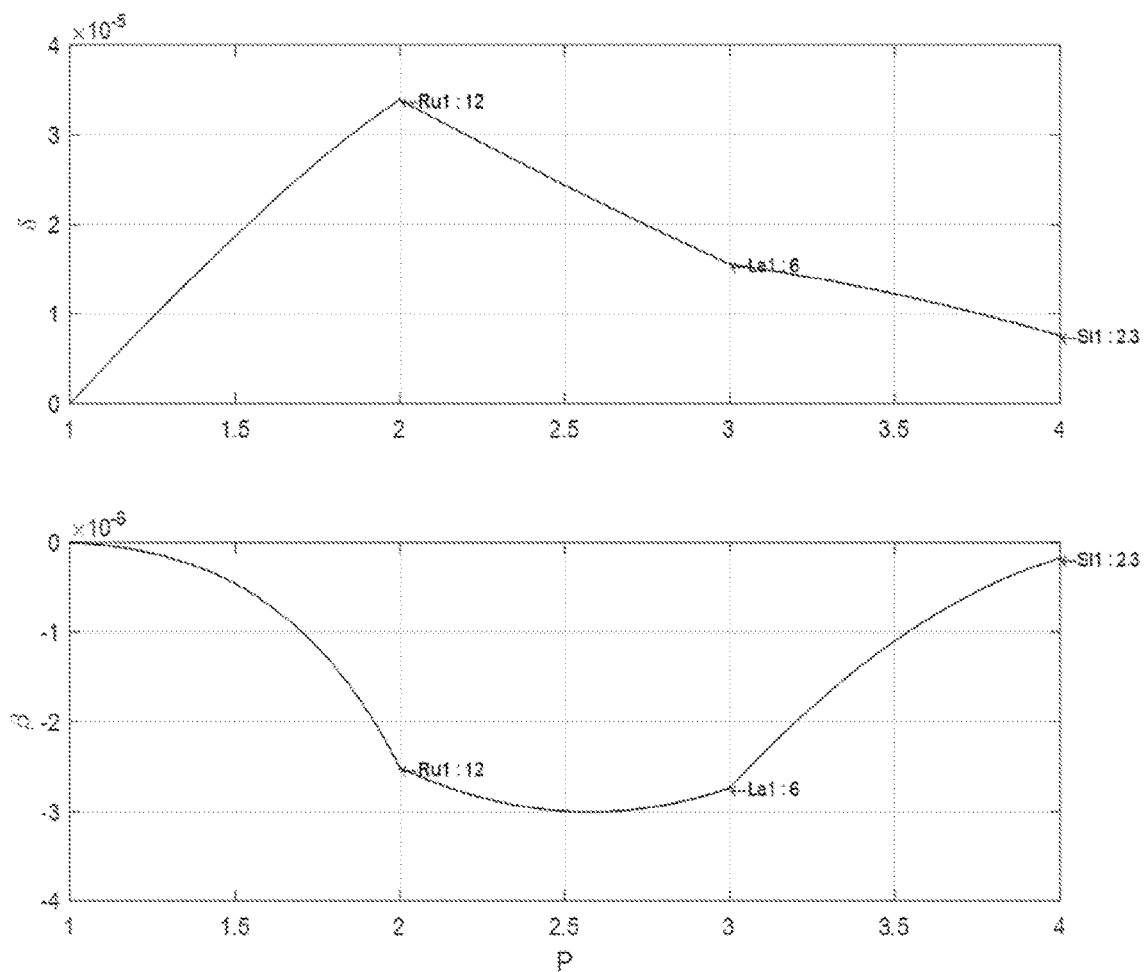
FIG. 4 shows the real (upper graph) and imaginary (lower graph) optical constants as a function of P value for the example of FIG. 1.

This is illustrated in FIG. 4, in which the top graph shows the real part of the refractive index of a material as a function of the value P and the lower graph shows the imaginary part of the refractive index of a material as a function of the value P, for the same materials as in the example above where P=1 indicates air, P=2 indicates ruthenium, P=3 indicates lanthanum and P=4 indicates silicon.

In practice, the real and imaginary parts of the refractive index may be calculated for the relevant materials before carrying out the fit and these values are stored in tabular form in refractive index tables 22 in computer 10 as representations of the real and imaginary values as a function of the value of P.

The set of N values of $P_j$ make up a vector P.

The calculation finds the specific vector $\tilde{P}$ that satisfies the condition $$\chi^2(\tilde{P}) = \min \chi^2(P). \tag{5}$$

i.e. which optimizes the goodness of fit presented as the sum of squares of the measured and simulated values of the GIXRR measurements u $$\chi^2 = \frac{1}{N-l} \left( \sum_\theta u^2(\theta, P) \right), \tag{6}$$

$$u(\theta, P) = \frac{I_{calc}(\theta, P) - I_{exp}(\theta)}{\sigma(\theta)}, \tag{7}$$

where N is a number of measured data points, θ is angle of incidence in GIXR measurements and $I_{calc}(\theta, P)$—calculated intensity of GIXRR, $I_{exp}(\theta, P)$—measured intensity of GIXRR, $\sigma(\theta)$—uncertainty of GIXRR measurement, l—number of the fit parameters.

In some examples, other parameters may be fitted. In particular, in some cases it may be necessary to include the density of the pure material layers as a fit parameter. The total thickness may also be a fitting parameter.

A vector p (using a small letter) will be used to represent all the fitting parameters, and $p_i$ will be used to represent individual fitting parameters from this vector.

It will be appreciated that in these cases exactly the same approach as above may be used, with P being replaced by p.

In a realistic multilayer structure, the optical constant profile is a smooth function and for this reason no large jumps in $n_i$ should be allowed from one sublayer to the next one. To incorporate this smoothness in the optimization procedure, in a further development of the method above a regularization coefficient $R_{reg}$ is added to the $\chi^2$ merit function $\tilde{X}^2 = \chi^2 + R$ where $R = \lambda \Sigma_{i=2}^{N-1} (2P_i - P_{i-1} - P_{i+1})^2$ where $N_A$ is the length of the vector x, r is a small number—the regularization parameter that specifies the degree of profile smoothness. The first term governs the continuity within the period, and the second and third set continuity on its borders. The same smoothening was applied for the top and bottom part of the structure.

It will be noted that the above formulae require the calculation of a calculated value of the intensity as a function of θ, and of course also as a function of the vector P (or in embodiments p).

For the X-ray reflectivity simulation we used the Abeles matrix approach optimized for modelling of the periodic multilayer structures.

In order to solve the optimization problem of Eq. (2) a Levenberg-Marquardt algorithm was used. Standard deviations of reconstructed parameters were calculated by the least squares method as in {Yakunin, 2014 #210} (Yakunin et al., 2014).

The strength of the method lies in the fact that a single real parameter can represent both the real and imaginary parts of the refractive index using a single variable that can represent multiple compositions from the multiple layers on the substrate. The real and imaginary parts of the refractive index of each sub-layer match a real potential composition, which forces the fitting algorithm to represent a true potential reality. The definition of P automatically assure that Karmers-Kroning relationship between real and imaginary parts of optical constant are satisfied. This constraint makes the fitting possible and convergent where other approaches simply do not work.

In particular, the method can easily cope with absorbing samples having significant imaginary parts in the refractive index which were simply ignored in some prior approaches. This improved representation of physical reality improves results.

If the number of sub-layers is too large, there are too many fitting parameters and this can lead to poor fits and errors in the results. If on the other hand, the number of sub-layers is too small, then the model does not have enough resolution to accurately model the measured data and again poor fits result.

An estimate of the optimal number of sub-layers $N_{opt}$ may be obtained from $$\Delta z_{opt} = \frac{1}{2} \frac{2\pi}{q_{max}} = \frac{\lambda}{4 \sin\theta_{max}} (*) \text{ where} \quad (8)$$

$$N_{opt} = \frac{L}{\Delta z_{opt}} \quad (9)$$

where $\theta_{max}$ is the highest measured angle and $\lambda$ the wavelength of X-rays used.

In specific cases when interfaces are too complex $\Delta z$ can be reduced.

The method is not just applicable to small numbers of layers but also has particular application to periodic structures repeating several periods.

Note that the method uses a parameterisation that can cope with absorption, therefore giving good results even in cases that prior methods may fail with. If necessary several lamellas can be foresed to have the same optical constants to mimic the layer with fixed density and avoid unnecessary increase of fitting parameters.

As an outcome of the data analysis an array of fit parameters p is obtained. To calculate the optical constant profile the optical constants are retrieved from best fit parameters p. This can be done be done by calling up the vector P and calculating the optical constant profile n using formulas (4) or retrieving the profile from a look up table. If a standard thin film parameters like layer thicknesses, densities and roughnesses have to be determined this can be done by fitting a standard parameterized profile, parameterised with a set of profile parameters, to the obtained optical constant profile. In this approach, a user can test various profile shapes of which the most common are sine, linear, or error function, amongst others and if necessary introduce interlayers to model interface compound formation.

Experiment

Figure 5:
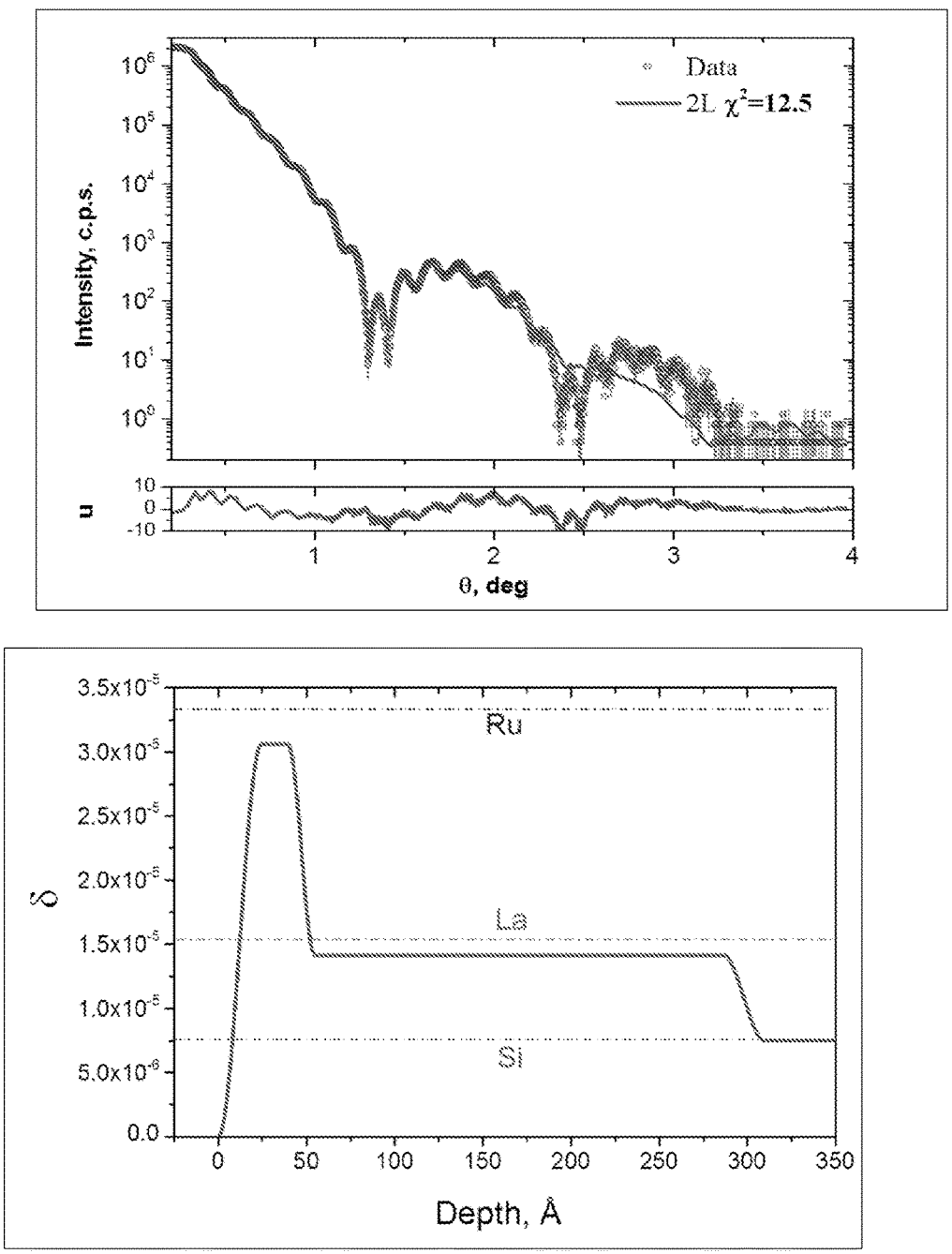
FIG. 5 shows a fit to experimental data using a comparative method.
Figure 6:
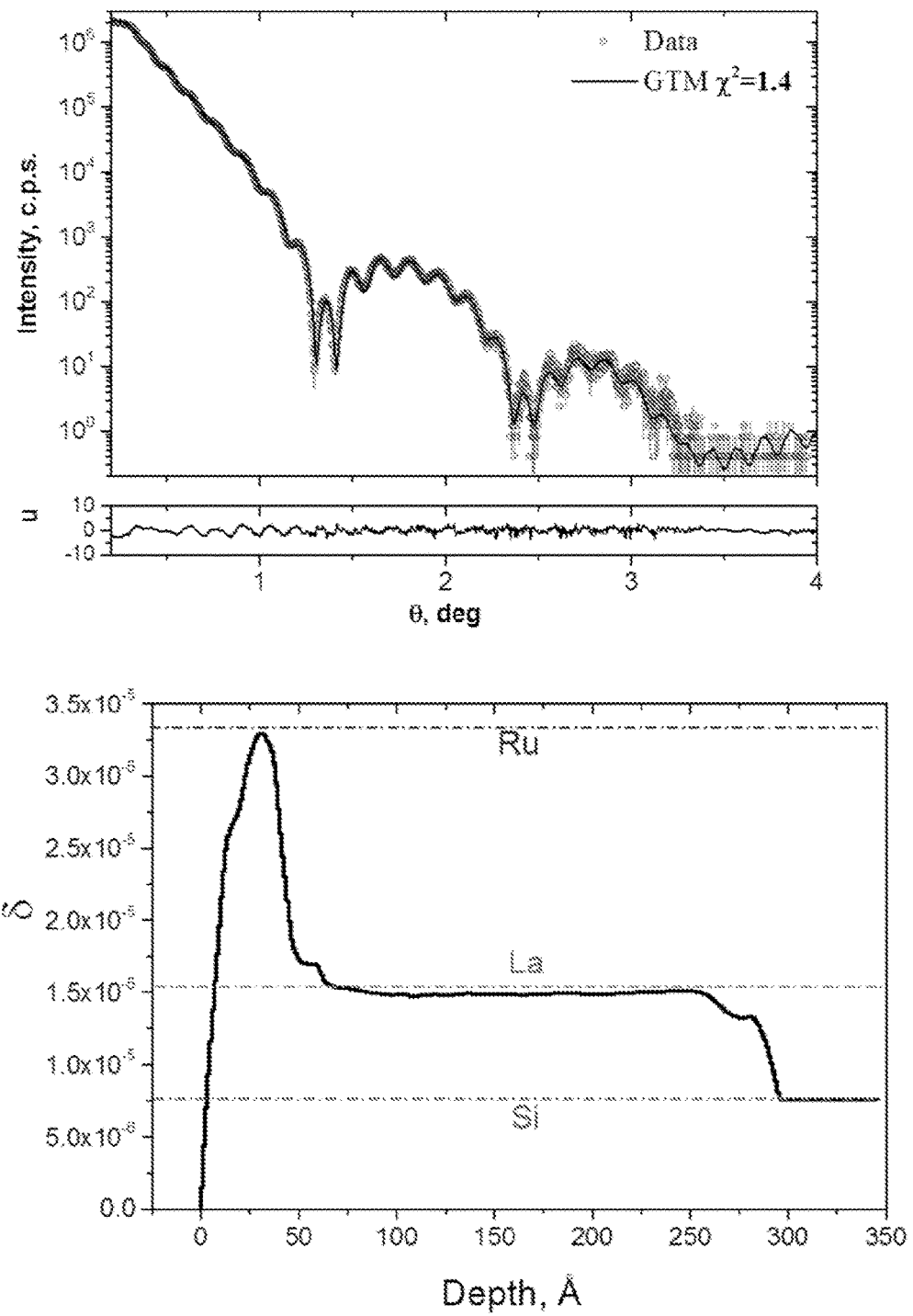
FIG. 6 shows a fit to the same experimental data using the method of the invention.

FIGS. 5 and 6 illustrate experimental data and fit lines for the example above, air on ruthenium on lanthanum on silicon.

The inventors first tried to fit to the measured data using a model according to a comparative example which had a layer of ruthenium on a layer of lanthanum on a layer of silicon. It was possible to obtain a reasonable fit for small angles but not for angles beyond 1° or 2°. The resulting $\chi^2$ value was a poor 12.5. The fit is shown in FIG. 5A and the resulting δ value profile in FIG. 5B.

The inventors then fit to the graph using a model according to the invention with a plurality of thin layers each of thickness 5.5 Å. A much better fit was obtained giving a $\chi^2$ value of 1.4, showing a reasonable fit to the measured data. FIG. 6A shows the fit and FIG. 6B shows the measured data.

Note how the method automatically results in a model that can cope with interface layers mixing the adjacent materials without the need for these to be preselected by the user. The result simply emerges from the automatic model.

Variations

In some cases, the method as described above may have difficulty in fitting to the entire curve in one step if the initial model of the vector P is too far from the optimal value. In this case, the method may be applied by fitting to the curve in segments as described in.

Figure 7:
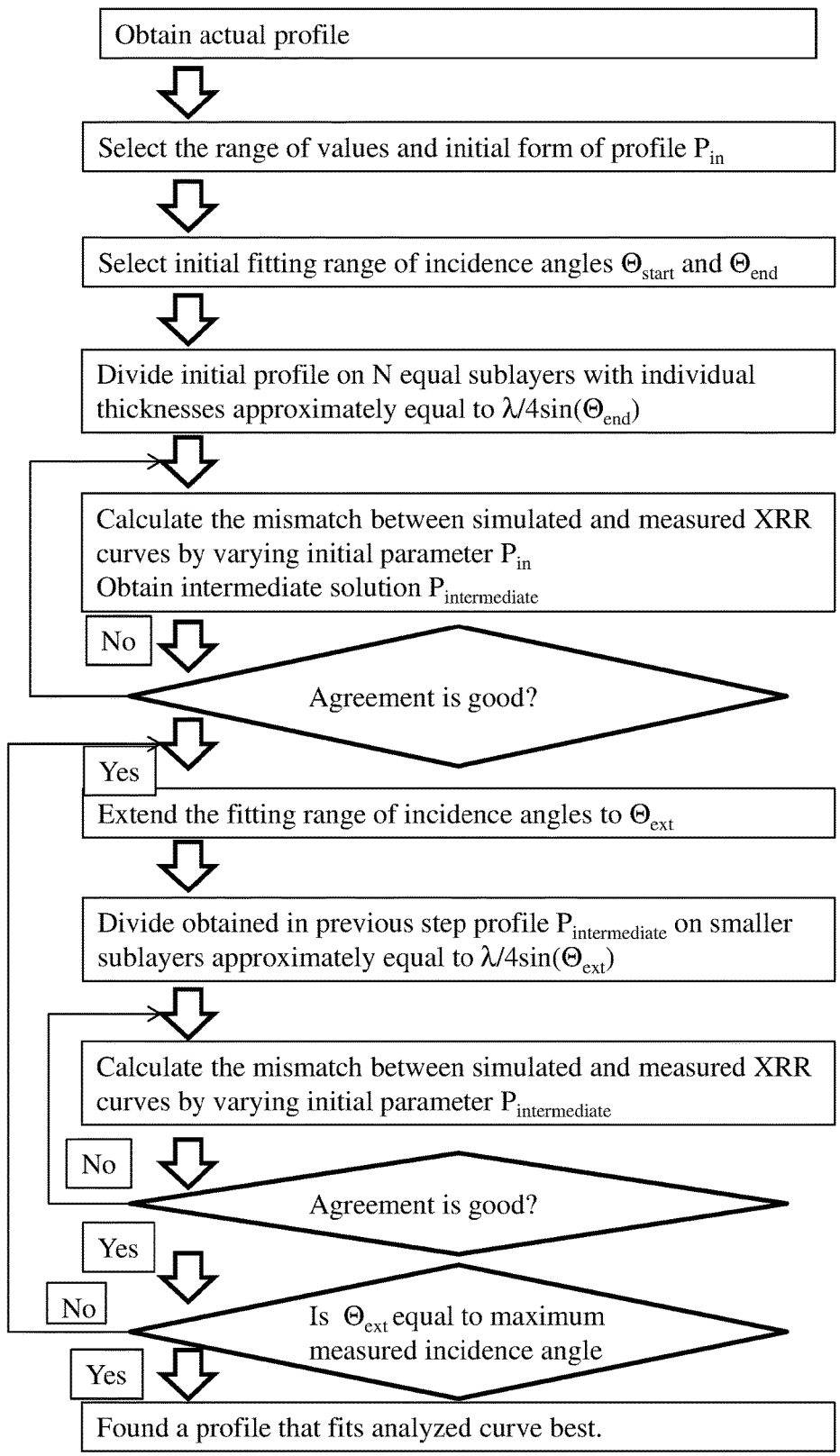
FIG. 7 is a flowchart of the method of the invention.

In detail, the method is described in the flow chart of FIG. 7.

As can be seen from the flow chart, the method starts by fitting in a limited range of angles and using smaller number of sublayers as presented in equations (8) and (9) and when a fit is obtained over that range the range of angles is extended and number of sublayers is increased.

Further, note that the method described above uses a particular representation of the values $P_j$ and variations to this representation are possible.

In particular, all that is required is that some specific values represent pure materials for the ordered list—these may be referred to as index values. Intermediate values and that intermediate values between these index values represent intermediate compositions. Accordingly, in more general terms, before the fitting step an ordered list of the plurality of physical materials in the stack is provided, and for each physical material a respective defined index value is defined, wherein the defined index values monotonically increase or monotonically decrease along the ordered list. Then, the parameter $P_i$ has values that are defined (a) to represent the respective physical material when the parameter $P_i$ has one of the defined index values; and (b) when the value $P_i$ lies between a pair of defined index values, to represent a composition that is a mixture of the physical materials of the pair of index values, the value of $P_i$ monotonically changing from the index value of a first physical material of a pair to the index value of the other physical material of the pair as the composition changes from pure first physical material to pure second physical material.

(c) the optical constant of lamella I can be found either by calculating using define formula that connects optical constant with Pi or by taking the value or interpolating between nearest values from look up table.

In the embodiments defined above, the index values are simply the respective integer, with air being given the index value 1 and subsequent layers starting from the top layer given the index value 2, 3 and so on. It will be appreciated that it would also be possible to give air the index value 0 and start at 1 from the top layer, or for example to give the top layer an index value 1, the next layer an index value 1001, the next layer an index value 2001 etc. Normally, real arithmetic will be used with the intermediate values being represented by real numbers since the representation should preferably be smooth but by picking sufficiently large index values integer arithmetic may also be used.

Further, note that the values of the parameter P may be either positive or negative.

The invention claimed is:

1. A method of measuring properties of a thin film stack made up of known physical materials and interfaces between the physical materials, the method comprising:

defining an ordered list of the plurality of physical materials in the stack, and defining for each physical material a respective defined index value, wherein the defined index values monotonically increase or monotonically decrease along the ordered list;

capturing a measured grazing index X-ray reflectivity curve of intensity against angle for a range of angles; and setting up an array of N sub-layers (j) representing the thin film stack, each element of the array of sub-layers having a defined parameter $P_j$ representing the composition of that sub-layer;

fitting the parameters $P_j$ so that a calculated grazing incidence X-ray reflectivity curve against angle as a function of the parameters $P_j$ most accurately matches the measured grazing index X-ray reflectivity curve against angle over the range of angles to obtain fitted parameters $\tilde{P}_j$;

and outputting a measure of the composition of the thin film stack based on the fitted parameters $\tilde{P}_j$;

wherein the parameters $P_j$ have values that are defined:

(a) to represent the respective physical material when the parameter $P_j$ has one of the defined index values; and (b) when the value $P_j$ lies between a pair of defined index values, to represent a composition that is a mixture of the physical materials of the pair of index values, the value of $P_j$ monotonically changing from the index value of a first physical material of a pair to the index value of the other physical material of the pair as the composition changes from pure first physical material to pure second physical material.

2. A method according to claim 1, wherein:

the defined index values are integers representing the position of the physical material in the list, and non-integer values x represent a composition having a fraction (1-frac ($P_j$)) of the material represented by the index value |x|; and a fraction frac ($P_j$) of the material represented by the index value |x|+1.

3. A method according to claim 1, wherein the step of fitting the parameters $P_j$ comprises minimising the value of the sum of squares of the residuals obtained by subtracting the measured grazing index reflective curve from the calculated grazing incidence reflectivity curve for each measured angle.

4. A method according to claim 3, wherein a Levenberg Marquardt algorithm is used to carry out the step of minimising.

5. A method according claim 1, wherein the step of fitting the parameters $P_j$ represented as a vector P comprises minimising the value of $$\chi^2 = \frac{1}{N-l}\left(\sum_\theta u^2(\theta, P)\right), \text{ where } u(\theta, P) = \frac{I_{calc}(\theta, P) - I_{exp}(\theta)}{\sigma(\theta)},$$

where N is a number of measured data points, θ is the angle of incidence in GIXRR measurements, $I_{calc}(\theta, P)$ is the calculated intensity of GIXRR, $I_{exp}(\theta, P)$ is the measured intensity of GIXRR, σ(θ)—uncertainty of GIXRR measurement, and l is the number of the fit parameters.

6. A method according to claim 1, wherein the step of fitting the parameters $P_j$ includes fitting the parameters as elements of a vector P, the method comprising minimising the value of $$\chi^2 = \frac{1}{N-l}\left(\sum_\theta u^2(\theta, P)\right) + R_{reg}.$$

$$\text{where } u(\theta, P) = \frac{I_{calc}(\theta, P) - I_{exp}(\theta)}{\sigma(\theta)},$$

where N is a number of measured data points, θ is the angle of incidence in GIXRR measurements, $I_{calc}(\theta, P)$ is the calculated intensity of GIXRR, $I_{exp}(\theta, P)$ is the measured intensity of GIXRR, σ(θ)—uncertainty of GIXRR measurement, and l is the number of the fit parameters; and $$R = \lambda \sum_{i=2}^{N-1}(2p_i - p_{i-1} - p_{i+1})^2$$

where $N_A$ is the length of the vector x, and r is a regularization parameter that specifies the degree of profile smoothness.

7. A method according to claim 1, further comprising providing a representation of the real part of the refractive index for a material represented by $P_j$ as a function of the value of $P_j$ and a representation of the imaginary part of the refractive index for a material represented by $P_j$ as a function of the value of $P_j$;

wherein the calculated grazing index reflectivity values are calculated using the refractive index values obtained from the values of $P_j$ using the representation of the real part and the representation of the imaginary part.

8. A method according to claim 1, wherein the number of sublayers is within 30% of $N_{opt}$ given by:

$$N_{opt} = \frac{L}{\Delta z_{opt}} \text{ where } \Delta z_{opt} = \frac{1}{2}\frac{2\pi}{q_{max}} = \frac{\lambda}{4\sin\theta_{max}},$$

$\theta_{max}$ is the highest measured angle and $\lambda$ the wavelength of X-rays used.

9. A method according to any claim 1, wherein the method comprises:

fitting the measured grazing index X-ray reflectivity curve of intensity against angle for a first range of angles up to a first upper angle; and repeating the step of fitting the measured grazing incidence X-ray reflectivity curve of intensity against angle for at least one subsequent range of angles up to at least one respective upper angle, wherein each subsequent range of angles has a higher upper angle than on the preceding step.

10. A method according to claim 1, further comprising calculating at least one of the real and imaginary parts of the refractive index at least one depth from the fitted parameters $\tilde{P}_j$, and outputting the calculated refractive indices.

11. A method according to claim 1, further comprising calculating thin film parameters such as -layer thicknesses, densities and roughnesses from the fitted parameters $\tilde{P}_j$, by defining a profile of the layers of the thin film stack with at least one variable profile parameter and varying the variable profile parameter to fit to the fitted parameters $\tilde{P}_j$.

* * * * *